US00PP17626P2

(12) United States Plant Patent
Bernuetz

(10) Patent No.: US PP17,626 P2
(45) Date of Patent: Apr. 17, 2007

(54) ***XEROCHRYSUM* PLANT NAMED 'OHDREJUMWHI'**

(50) Latin Name: *Xerochrysum bracteatum*
Varietal Denomination: Ohdrejumwhi

(75) Inventor: Andrew Bernuetz, Silverdale (AU)

(73) Assignee: Bonza Botanicals Pty., Ltd., Sydney (AU)

( * ) Notice: Subject to any disclaimer, the term of this patent is extended or adjusted under 35 U.S.C. 154(b) by 13 days.

(21) Appl. No.: 11/270,068

(22) Filed: Nov. 9, 2005

(51) Int. Cl.
*A01H 5/00* (2006.01)

(52) U.S. Cl. ..... Plt./263

(58) Field of Classification Search ..... Plt./263
See application file for complete search history.

(56) References Cited

PUBLICATIONS

European Plant Breeders' Rights application No. 2005/2001 filed Oct. 25, 2005.

*Primary Examiner*—Kent Bell
*Assistant Examiner*—Annette H Para
(74) *Attorney, Agent, or Firm*—Audrey Charles

(57) ABSTRACT

A new and distinct cultivar of *Xerochrysum* plant named 'Ohdrejumwhi' characterized by its white-colored involucral bracts and yellow-orange-colored disc florets, dark green-colored foliage, good basal branching character, and upright growth habit.

2 Drawing Sheets

Latin name of genus and species of plant claimed: *Xerochrysum bracteatum* (previously *Bracteantha bracteata*).
Variety denomination: 'Ohdrejumwhi'.

BACKGROUND OF THE INVENTION

The present invention relates to a new and distinct cultivar of *Xerochrysum* plant botanically known as *Xerochrysum bracteatum* and hereinafter referred to by the cultivar name 'Ohdrejumwhi'.

The new cultivar originated in a controlled breeding program in Winmalee, Australia during 2002. The objective of the breeding program was the development of *Xerochrysum* cultivars with attractive flower colors and vigorous upright growth habit.

The female (seed) parent of the new cultivar was the proprietary *Xerochrysum bracteatum* breeding selection designated 02-7, not patented, characterized by its white-colored involucral bracts, dark green-colored foliage, and medium compact growth habit. The male (pollen) parent of the new cultivar was 'OHB003790', U.S. Plant Pat. No. 15,629, characterized by its yellow-colored involucral bracts, medium to dark green-colored foliage, and compact upright growth habit. The new *Xerochrysum* was discovered and selected by the inventor as a single flowering plant within the progeny of the above stated cross-pollination during February 2003 in a controlled environment at Winmalee, Australia.

Asexual reproduction of the new cultivar by terminal stem cuttings since February 2003 at Winmalee, Australia and West Chicago, Ill. has demonstrated that the new cultivar reproduces true to type with all characteristics, as herein described, firmly fixed and retained through successive generations of such asexual propagation.

SUMMARY OF THE INVENTION

The following characteristics of the new cultivar have been repeatedly observed and can be used to distinguish 'Ohdrejumwhi' as a new and distinct cultivar of *Xerochrysum* plant:

1. White-colored involucral bracts and yellow-orange-colored disc florets;
2. Dark green-colored foliage;
3. Good basal branching character; and
4. Upright growth habit.

Plants of the new cultivar differ from plants of the female parent primarily in growth habit and from plants of the male parent primarily in flower color and growth habit.

Of the many commercially available *Xerochrysum* cultivars known to the inventor, the most similar in comparison to the new cultivar is the male parent 'OHB003790', U.S. Plant Pat. No. 15,629. However, in side by side comparisons, plants of the new cultivar differ from plants of 'OHB003790' in the following characteristics:

1. Plants of the new cultivar have more involucral bracts than plants of 'OHB003790';
2. Plants of the new cultivar have more disc florets than plants of 'OHB003790'; and
3. Plants of the new cultivar have a different involucral bract color from plants of 'OHB003790'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Ohdrejumwhi'. The plants were grown in 10 cm pots for 9 weeks in a greenhouse at West Chicago, Ill.

DETAILED BOTANICAL DESCRIPTION

Figure 1:
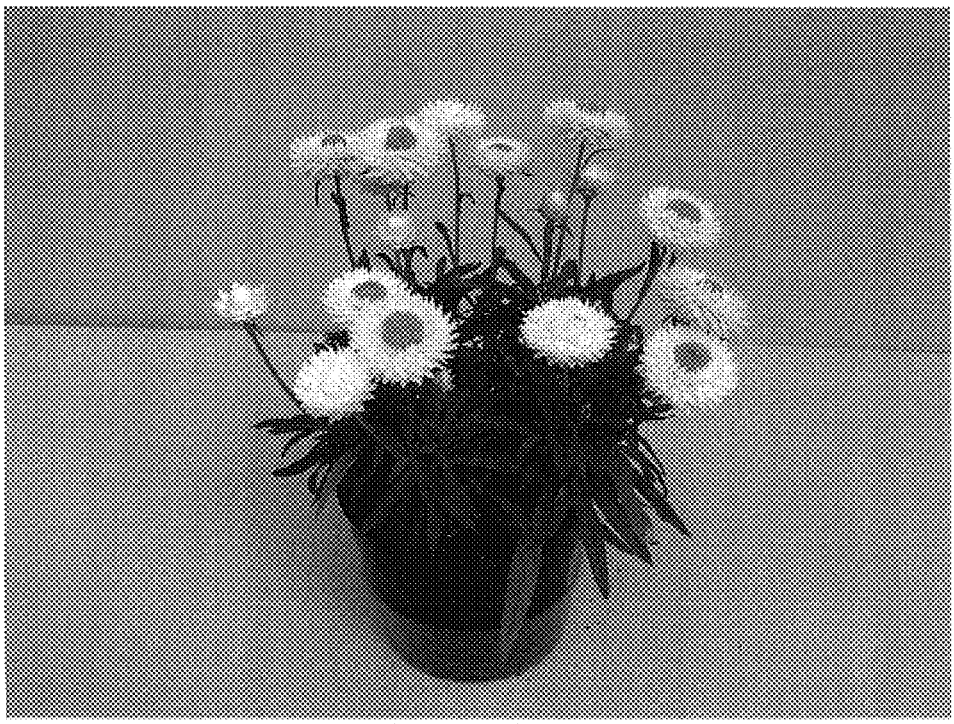
FIG. 1 illustrates a side view of the overall growth and flowering habit of 'Ohdrejumwhi'.
Figure 2:
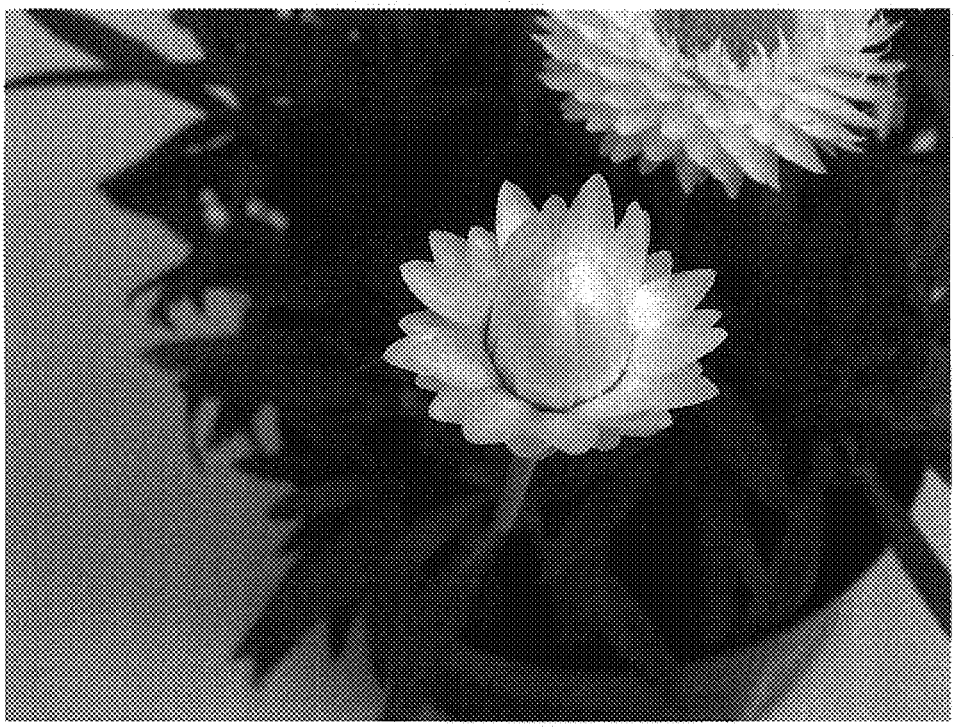
FIG. 2 illustrates a close-up view of a single inflorescence of 'Ohdrejumwhi' with some open involucral bracts.
Figure 3:
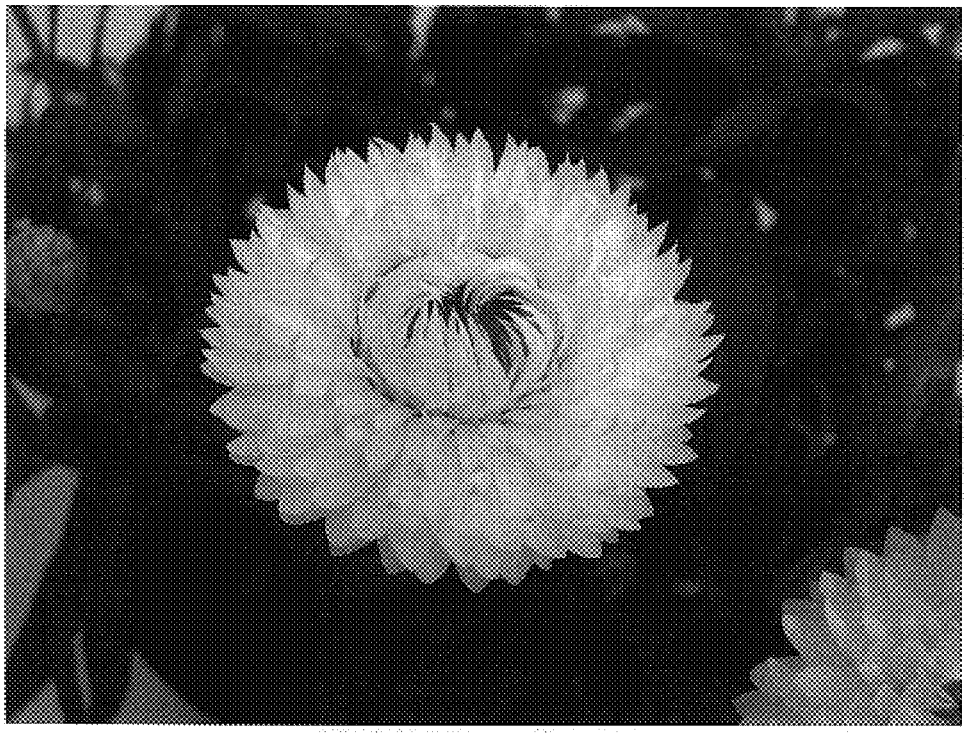
FIG. 3 illustrates a close-up view of a single inflorescence of 'Ohdrejumwhi' with most of the involucral bracts open.
Figure 4:
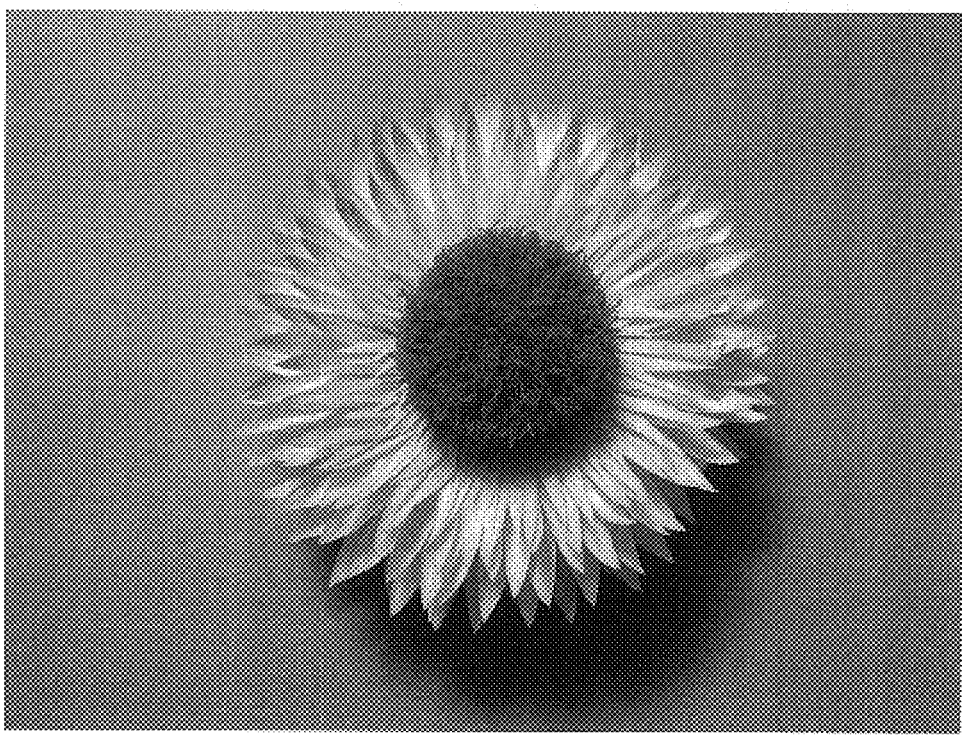
FIG. 4 illustrates a close-up view of a single inflorescence of 'Ohdrejumwhi' with all involucral bracts and disc florets fully open.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on Jul. 27, 2005 between 3:00 p.m. and 4:00 p.m. under natural light conditions, in West Chicago, Ill.

The following descriptions and measurements describe plants produced from cuttings taken from stock plants and grown in a double polycarbonate-covered greenhouse under conditions comparable to those used in commercial practice. The plants were grown at West Chicago, Ill. in 10 cm pots for 9 week utilizing a soilless growth medium. Greenhouse temperatures were maintained at approximately 65° F. to 75° F. (18° C. to 24° C.) during the day and approximately 55° F. to 60° F. (13° C. to 16° C.) during the night. Greenhouse light levels of approximately 5,000 to 8,000 footcandles were maintained during the day.

Botanical classification: *Xerochrysum bracteatum* cultivar Ohdrejumwhi.

Parentage:

*Female parent.*—Proprietary *Xerochrysum bracteatum* breeding selection designated 02-7, not patented.

*Male parent.*—'OHB003790', U.S. Plant Pat. No. 15,629.

Propagation:

*Type cutting.*—Terminal stem.

*Time to initiate roots.*—Approximately 6 to 9 days.

*Time to produce a rooted cutting.*—Approximately 21 days.

*Root description.*—Fine, fibrous.

*Rooting habit.*—Freely branching.

Plant description:

*Crop time.*—Approximately 6 to 8 weeks from a rooted cutting.

*Growth habit.*—Freely basal branching, vigorous.

*General appearance.*—Upright.

*Size.*—Height from soil level to top of plant plane: Approximately 19.4 cm. Height from top of soil to top of foliage: Approximately 13.4 cm. Width: Approximately 34.1 cm.

*Branch.*—Quantity per plant: Approximately 15 main branches with lateral branches potentially forming at every node. Length: Approximately 6.3 cm. Diameter: Approximately 3.3 mm. Texture: Villous. Color: 144B. Internode length at center of branch: Approximately 1.4 cm.

*Foliage.*—Quantity of leaves per lateral branch: Approximately 11. Type: Simple. Fragrance: None. Arrangement: Alternate. Aspect: At acute angle with apex downturning. Shape: Elliptic. Apex: Acuminate. Base: Sessile. Margin: Entire. Venation pattern: Parallel. Length: Approximately 8.7 cm. Width: Approximately 1.2 cm. Texture of upper surface: Glabrous. Texture of lower surface: Glabrous with short, stiff hairs along the midvein. Color of upper surface of mature foliage: Closest to 139A with venation of 145B and 144B on either side of base of midvein. Color of lower surface of mature foliage: Closest to 146A with venation of 145B.

Flowering description:

*Flowering habit.*—'Ohdrejumwhi' is freely flowering under outdoor growing conditions with substantially continuous blooming from spring through autumn and year round in greenhouse environment.

*Time to first flower.*—Approximately 14 weeks after sticking of unrooted cutting.

*Lastingness of individual bloom.*—Approximately 18 days.

Inflorescence description:

*Appearance.*—Type: Double, composite. Aspect: Facing outward or upward. Arrangement: Terminal, solitary.

*Quantity per plant.*—Approximately 4 open enough for disc florets to be showing. Approximately 12 with at least two rows of bracts open.

*Fragrance.*—None.

*Peduncle.*—Strength: Strong. Aspect: Erect. Length: Approximately 8.3 cm. Diameter: Approximately 2.5 mm. Texture: Tomentose. Color: 144B.

Flower description:

*Shape/size.*—Hemispherical when ray florets are fully open. Inflorescence diameter: Approximately 4.7 cm. Inflorescence depth: Approximately 2.1 cm. Disc diameter: Approximately 1.6 cm. Disc depth: Approximately 5.0 mm. Receptacle diameter: Approximately 2.3 cm. Receptacle color: 145C.

*Bud rate of opening.*—Generally takes approximately 3 weeks for bud to progress from first color to fully open flower.

*Bud just before opening.*—Quantity per plant: Approximately 4. Shape: Ovate. Length: Approximately 1.1 cm. Diameter: Approximately 9.5 mm. Texture: Glabrous. Color: Lighter than 155B.

*Involucral bracts.*—Quantity: Approximately 297 per inflorescence. Arrangement: Imbricate, in approximately 16 whorls. Aspect: Slightly cupped with tips turning upward. Shape: Lanceolate. Apex: Acute. Base: Truncate. Margin: Entire. Length: Ranges from approximately 1.1 cm for innermost bracts to approximately 1.8 cm for outermost bracts. Width: Varies from approximately 5.2 mm for outmost bracts to 6.0 mm for innermost bracts. Texture of upper and lower surfaces: Papery, glabrous. Color of upper and lower surfaces when fully open: 155A transitioning to 146A at base.

*Disc florets.*—Quantity: Approximately 1,200. Arrangement: Massed in center of inflorescence. Shape: Tubular. Margin: Entire. Length: Approximately 1.0 cm. Width: Approximately 1.0 mm. Color: 21A.

*Reproductive organs.*—Androecium: Present on disc florets only. Stamen number: Approximately 5. Anther shape: Linear. Anther length: Approximately 3.0 mm. Anther color: 13A. Pollen amount: Abundant. Pollen color: 14A. Gynoecium: Pistil number:

1. Pistil length: Approximately 1.1 cm. Stigma shape: Two-parted, linear. Stigma length: Approximately 2.0 mm. Stigma color: 21A. Style length: Approximately 8.0 mm. Style color: Lighter than 21A, translucent. Ovary diameter: Approximately 1.0 mm. Ovary color: 145D.

Seed and fruit production: Neither seed nor fruit production has been observed.

Disease and pest resistance: Resistance to pathogens and pests common to *Xerochrysum* has not been observed.

What is claimed is:

1. A new and distinct cultivar of *Xerochrysum* plant named 'Ohdrejumwhi', substantially as herein shown and described.

* * * * *